United States Patent

Magni et al.

[11] Patent Number: 5,808,051
[45] Date of Patent: Sep. 15, 1998

[54] PROCESS FOR PREPARING NEUROMUSCULAR BLOCKING AGENTS AND INTERMEDIATES USEFUL THEREFOR

[75] Inventors: Ambrogio Magni, Osnago; Paride Grisenti, Milan, both of Italy

[73] Assignee: Poli Industria Chimica, S.p.a., Milan, Italy

[21] Appl. No.: 958,456

[22] Filed: Oct. 27, 1997

Related U.S. Application Data

[62] Division of Ser. No. 761,631, Dec. 6, 1996.

[30] Foreign Application Priority Data

Dec. 22, 1995 [IT] Italy ............................... M195A2735

[51] Int. Cl.⁶ .............................. C07J 11/00; C07J 71/00
[52] U.S. Cl. ............................................. 540/76; 552/536
[58] Field of Search ........................... 540/76; 552/536

[56] References Cited

U.S. PATENT DOCUMENTS

| | | | |
|---|---|---|---|
| 3,097,200 | 7/1963 | Kincl | 540/95 |
| 3,169,093 | 2/1965 | Davis | 514/172 |
| 3,225,034 | 12/1965 | Hewett et al. | 540/5 |
| 3,238,194 | 3/1966 | Klimstra et al. | 540/95 |
| 3,380,886 | 4/1968 | Campbell et al. | 514/178 |
| 3,458,504 | 7/1969 | Clinton | 540/22 |
| 3,553,212 | 1/1971 | Hewett et al. | 540/96 |
| 3,872,091 | 3/1975 | Hewett et al. | 540/96 |
| 4,071,515 | 1/1978 | Tuba et al. | 540/96 |
| 4,101,545 | 7/1978 | Tuba et al. | 540/96 |
| 4,110,326 | 8/1978 | Tuba et al. | 540/77 |
| 4,177,190 | 12/1979 | Tuba | 540/96 |
| 4,179,507 | 12/1979 | Stenlake et al. | 514/308 |
| 4,237,126 | 12/1980 | Carlyle et al. | 514/176 |
| 4,297,351 | 10/1981 | Caryle et al. | 514/176 |
| 4,348,390 | 9/1982 | Kelder | 514/176 |
| 4,352,798 | 10/1982 | Phillips et al. | 514/177 |
| 4,353,898 | 10/1982 | Phillips et al. | 514/182 |
| 4,447,425 | 5/1984 | Carlyle et al. | 514/176 |
| 4,451,405 | 5/1984 | Phillips et al. | 514/171 |
| 4,497,805 | 2/1985 | Phillips et al. | 514/172 |
| 4,515,786 | 5/1985 | Phillips et al. | 514/182 |
| 4,891,366 | 1/1990 | Sleigh et al. | 514/176 |
| 4,894,369 | 1/1990 | Sliegh et al. | 514/176 |
| 5,030,633 | 7/1991 | Williams | 514/231.5 |
| 5,140,022 | 8/1992 | Chen | 514/212 |
| 5,190,924 | 3/1993 | Konteatis et al. | 514/19 |
| 5,229,511 | 7/1993 | Chen | 540/597 |
| 5,410,040 | 4/1995 | Tuba et al. | 540/96 |
| 5,418,226 | 5/1995 | Sliegh et al. | 514/176 |

FOREIGN PATENT DOCUMENTS

| | | |
|---|---|---|
| 1138605 | 1/1969 | United Kingdom . |
| 1398050 | 6/1975 | United Kingdom . |
| 1454749 | 11/1976 | United Kingdom . |

OTHER PUBLICATIONS

Xu et al., Youji Huaxue, vol. 9, pp. 451–454, 1989.
Douglas et al., "Preparation of Axial Alcohols and Olefins from Equatorial Alcohols," *J. Chem. Soc.* 340:1720–1723 (1959).
Glazier, "Bromination of 17–Oxo Steriods with Cupric Bromide," *J. Org. Chem.* 27:2937–2938 (1962).
Iriarte et al., "Steroids, LXV. A Synthesis of Androsterone," *J. Org. Chem.* 20:542–545 (1955).
Pento et al., "Rocurium Bromide," *Drugs of the Future* 19 (9) :841–844 (1994).
Sollman et al., "Alkoxylation of Steriods with Cuprie Bromide Alcohol," *Communications* 26:4180–4181 (1961).

Primary Examiner—Richard L. Raymond
Attorney, Agent, or Firm—Townsend and Townsend and Crew, LLP

[57] ABSTRACT

The present invention provides new process of preparing neuromuscular blocking agents. The process include preparing neuromuscular blocking agents using the compounds of formula I:

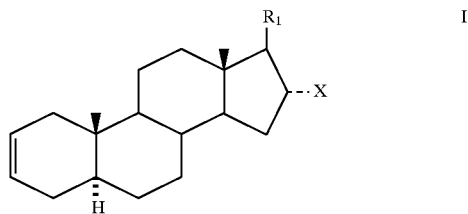

wherein $R_1$ is =O and X is halo; and formula II:

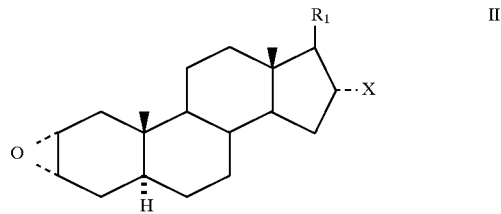

wherein $R_1$ and X are as defined above.

18 Claims, No Drawings

5,808,051

PROCESS FOR PREPARING NEUROMUSCULAR BLOCKING AGENTS AND INTERMEDIATES USEFUL THEREFOR

RELATED APPLICATIONS

The instant application is a division of U.S. patent application Ser. No. 08/761,631, filed 6 Dec. 1996, the disclosure of which is hereby incorporated by reference in its entirety.

FIELD OF THE INVENTION

The present invention relates to processes of preparing pharmaceutically active agents, and in particular to processes of preparing pharmaceutically active neuromuscular blocking agents.

BACKGROUND OF THE INVENTION

Neuromuscular blocking agents are employed in therapy as coadjuvants in surgical anaesthesia to obtain relaxation of skeletal muscles. Typically, therapy is performed by i.v. administration of a suitable dosage form. This dosage form may be administered by dissolving a freeze-dried powder, containing the active ingredient associated with some excipients, in water or another suitable solvent.

One neuromuscular blocking agents, vecuronium bromide, was first described in U.S. Pat. No. 3,553,212 to Hewett et al. Various formulations for neuromuscular blocking agents, including vecuronium bromide, have also been proposed.

Several processes have been proposed for the preparation of neuromuscular blocking agents. According to the method described in U.S. Pat. No. 3,553,212, neuromuscular blocking agents may be prepared by synthons obtained by reacting a 16α,17α-oxido, or a 17β-hydroxy-16-keto androstane with an amine at elevated temperature and pressure.

U.S. Pat. Nos. 4,101,545, 4,110,326, and 4,117,190 all to Tuba, et al. propose a process for preparing diamino androstanes which includes reacting a diepoxy androstane with a cyclic amine, followed by reduction to the 17β-hydroxy androstane.

There remains a need in the art for a new process of preparing diamino-androstane neuromuscular blocking agents.

SUMMARY OF THE INVENTION

Specifically, as a first aspect, the present invention provides a process for preparing a compound of Formula III:

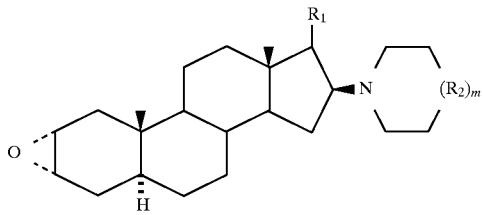

wherein $R_1$ is $=O$, $R_2$ is $>CH_2$, $>CHR_6$, $>CR_6R_6$, $>NH$, $>NR_6$, or $>O$, wherein each $R_6$ is independently lower alkyl, and m is an integer from 0 to 1. The process comprises reacting a compound of Formula II:

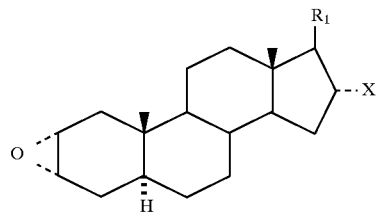

wherein X is halo, with a compound of Formula VI:

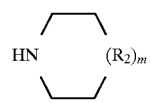

to produce the compound of Formula III.

As a second aspect, the present invention provides a second process for preparing a compound of Formula III. The process comprises the steps of: a) reacting a compound of Formula I:

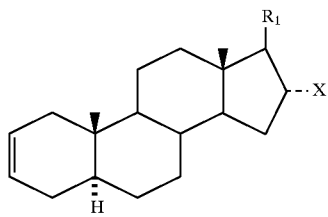

wherein X is halo, with a peracid in a nonpolar, aprotic solvent to produce a compound of Formula II, and b) reacting the compound of Formula II with a compound of Formula VI to produce the compound of Formula III.

As a third aspect, the present invention provides a process for preparing a compound of Formula IV:

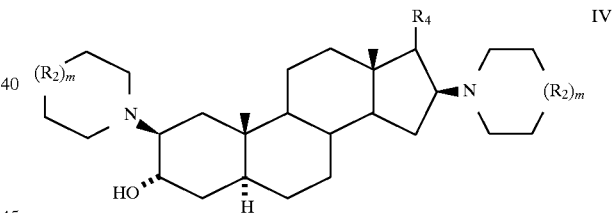

wherein each $R_2$ is independently $>CH_2$, $>CHR_6$, $>CR_6R_6$, $>NH$, $>NR_6$, or $>O$, wherein each $R_6$ is independently lower alkyl, each m is independently an integer from 0 to 1, and $R_4$ is $=O$ or $H(\beta\text{-OH})$. The process comprises the steps of a) reacting a compound of Formula II with a compound of Formula VI to produce the compound of Formula III; b) reducing the compound of Formula III with a reducing agent to produce a reduced intermediate; and c) reacting the reduced intermediate with a compound of Formula VI to produce the compound of Formula IV.

As a fourth aspect, the present invention provides another process for preparing a compound of Formula IV. The process comprises the steps of a) reacting a compound of Formula I with a peracid in a hydrophobic aprotic solvent to produce a compound of Formula II; b) reacting the compound of Formula II with a compound of Formula VI to produce the compound of Formula III; c) reducing the compound of Formula III with a reducing agent to produce a reduced intermediate; and then d) reacting the reduced intermediate with a compound of Formula VI to produce the compound of Formula IV.

As a fifth aspect, the present invention provides a process for preparing neuromuscular blocking agents. The process comprises the steps of a) reacting a compound of Formula II with a compound of Formula VI to produce the compound of Formula III; b) reducing the compound of Formula III with a reducing agent to produce a reduced intermediate; c) reacting the reduced intermediate with a compound of Formula VI to produce a compound of Formula IV d) acylating the compound of Formula IV with an acylating agent to produce a diacyloxy intermediate; and e) converting the diacyloxy intermediate to a mono- or di-quaternary amine salt thereof to produce the neuromuscular blocking agent.

As a sixth aspect, the present invention provides a second process for preparing neuromuscular blocking agents. The process comprises a) reacting a compound of Formula II with a compound of Formula VI to produce the compound of Formula III; b) reacting the compound of formula III with a compound of Formula VI to produce a compound of Formula IV; c) acylating the compound of Formula IV with an acylating agent to produce a monoacyloxy intermediate; d) reducing the monoacyloxy intermediate with a reducing agent to produce a reduced intermediate; e) acylating the reduced intermediate with an acylating agent to produce a diacyloxy intermediate; and f) converting the diacyloxy intermediate to a mono-quaternary amine salt thereof to produce the neuromuscular blocking agent.

As a seventh aspect, the present invention provides a process for preparing neuromuscular blocking agents. The process comprises a) reacting a compound of Formula II with a compound of Formula VI to produce the compound of Formula III; b) reducing the compound of Formula III with a reducing agent to produce a reduced intermediate; c) acylating the reduced intermediate with an acylating agent to produce a monoacyloxy intermediate; d) reacting the monoacyloxy intermediate with a compound of Formula VI to produce a compound of Formula XI:

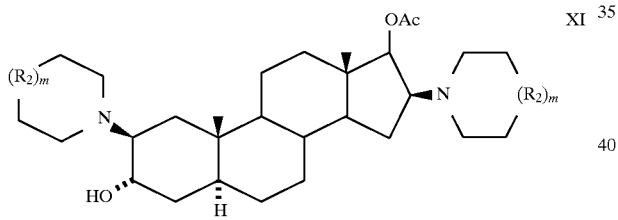

and e) converting the compound of Formula XI to a mono-quaternary amine salt thereof to produce the neuromuscular blocking agent.

As an eighth aspect, the present invention provides a process for preparing vecuronium bromide or pancuronium bromide. The process comprises the steps of a) reacting the compound of Formula I with metachloroperbenzoic acid in methylene chloride to produce a compound of Formula II; b) reacting the compound of Formula II with piperidine to produce the compound of Formula III; c) reducing the compound of Formula III with sodium borohydride to produce a reduced intermediate; d) reacting the reduced intermediate with piperidine to produce a compound of Formula IV; e) acylating the compound of Formula IV with an acylating agent selected from the group consisting of acetic acid, acetic anhydride, and mixtures thereof, to produce a diacyloxy intermediate; and f) converting the diacyloxy intermediate to a mono- or di-quaternary amine salt thereof to produce vecuronium bromide or pancuronium bromide.

As a ninth aspect, the present invention provides a compound of Formula I:

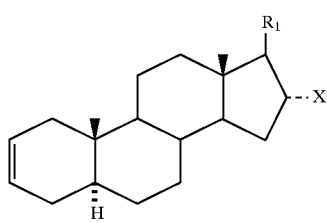

wherein $R_1$ is $=O$ and X is halo.

As an tenth aspect, the present invention provides a compound of formula II:

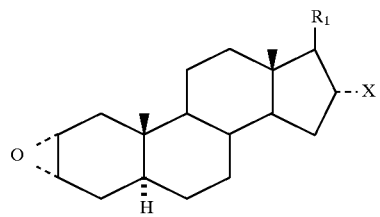

wherein $R_1$ is $=X$ and X is halo.

As a eleventh aspect, the present invention provides a process for preparing the compound of Formula I. The process includes 16α-halogenating a compound of Formula VIII:

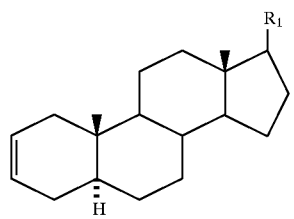

with copper(II)halide to produce the compound of Formula I.

As a twelfth aspect, the present invention provides a process for preparing the compound of Formula II. The process includes reacting a compound of Formula I with a peracid in a hydrophobic aprotic solvent.

The foregoing and other aspects of the present invention are explained in detail in the detailed description and examples set forth hereinbelow.

DETAILED DESCRIPTION OF THE INVENTION

As used herein, the term "lower alkyl" refers to linear branched or cyclic, saturated or unsaturated $C_{1-8}$ alkyls such as methyl, ethyl, propyl, iso-propyl, butyl, iso-butyl, t-butyl, pentyl, cyclopentyl, hexyl, cyclohexyl, and octyl. The term "halo" or "halogen" as used herein refers to any fluoro, chloro, bromo, or iodo. The term "OAc" in the formulas recited herein refers to the acyloxy group, $O-C(O)CH_3$, as is commonly used in the art.

The neuromuscular blocking agents which can be prepared according to the process of the present invention include the diamino-androstanes. Diamino-androstane neuromuscular blocking agents which can be prepared according to the process of the present invention includes compounds having the general formula X or X-A:

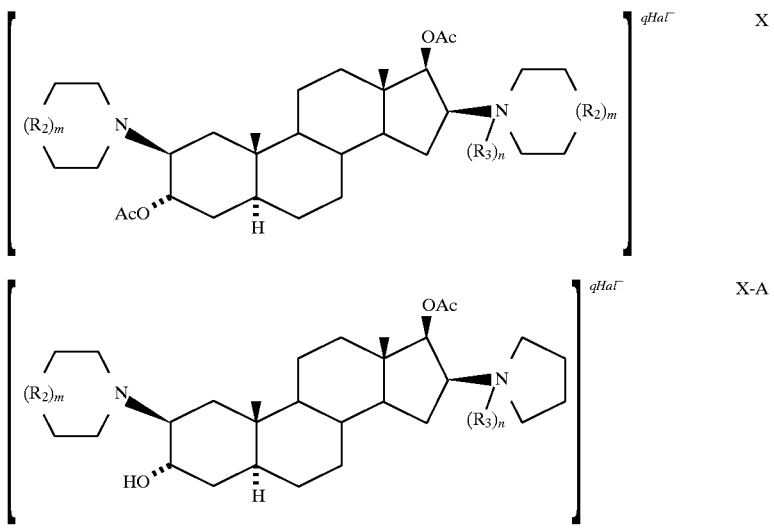

wherein each $R_2$ is independently $>CH_2$, $>CHR_6$, $>CR_6R_6$, $>NH$, $>NR_6$, or $>O$, wherein $R_6$ is loweralkyl, each m is independently an integer from 0 to 1, $R_3$ is lower alkyl, n is an integer from 0 to 1, $Hal^-$ is a halide ion, and q is 1 or 2. As used herein, when m is 0, $R_2$ is a direct bond between the carbon atoms to which it is attached. As used herein, when n is 0, $R_3$ is not present (i.e., it is replaced by H). Preferred diamino-androstane neuromuscular blocking agents include but are not limited to vecuronium bromide, pancuronium bromide, pipecurium bromide, rocuronium bromide, and Org-9487.

Essentially, the processes of the present invention involve the preparation of neuromuscular blocking agents using the new compounds of formula I:

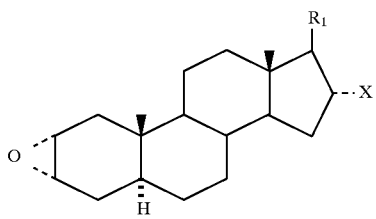

wherein $R_1$ is =O and X is halo; and the new compounds of formula II:

II wherein $R_1$ and X are as defined above.

More specifically, the neuromuscular blocking agents are prepared using the process of the present invention, according to any of Schemes 1, 2, or 3.

Scheme 1

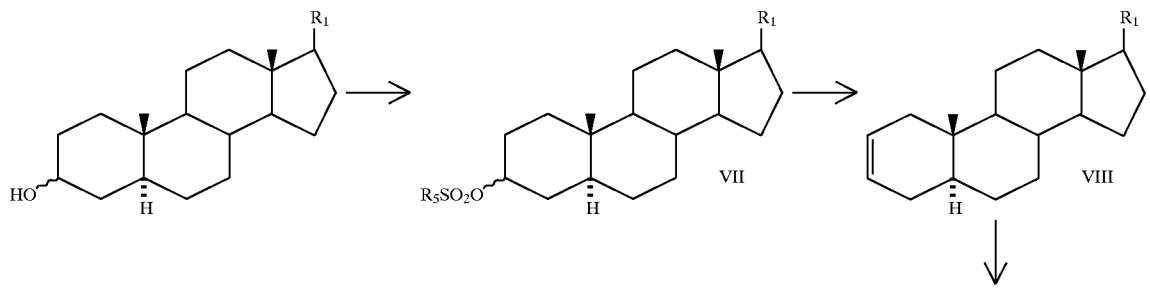

Scheme 1 -continued
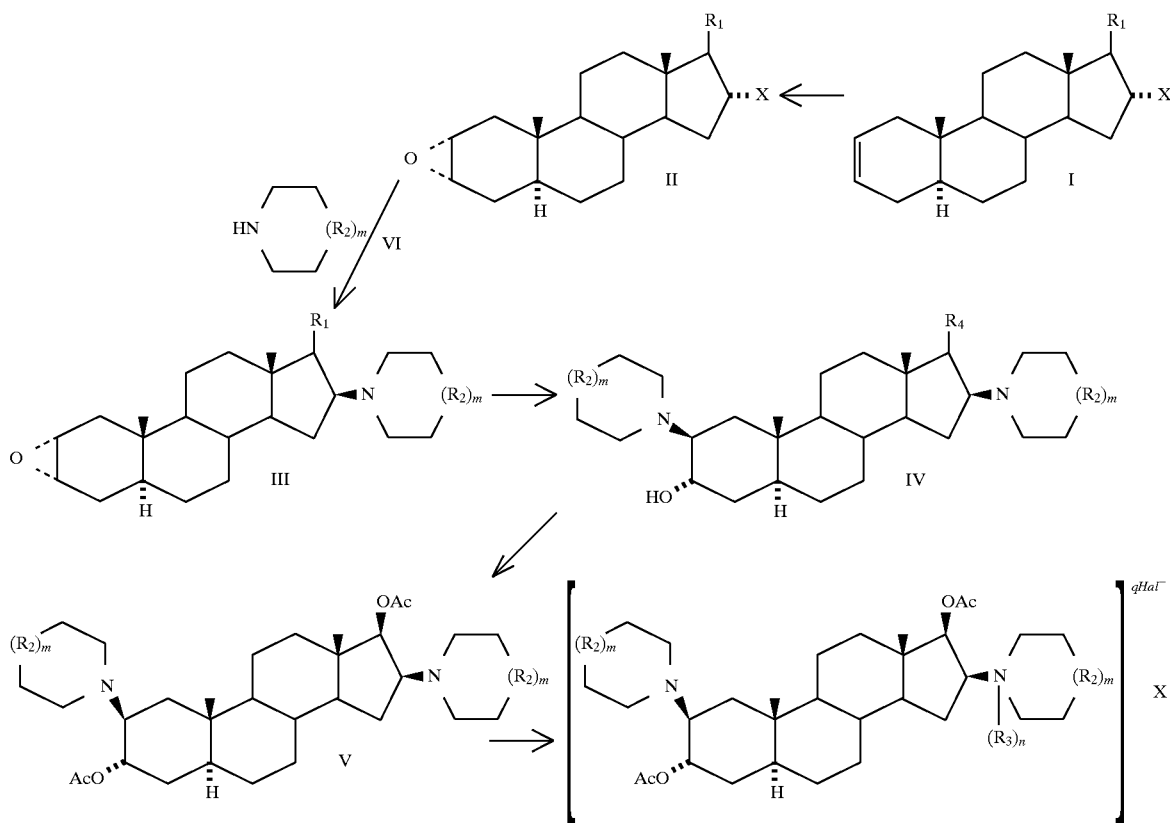
wherein $R_1$ is =), each $R_2$ is independently >$CH_2$, >$CHR_6$, >$CR_6R_6$, >NH, >$NR_6$, or >O, wherein each $R_6$ is independently lower alkyl, each m is independently an integer from 0 to 1, $R_3$ is lower alkyl, n is an integer from 0 to 1, X is halo, $Hal^-$ is a halide ion, and q is 1 or 2, $R_4$ is preferably H($\beta$-OH), and $R_5$ is methyl or p-tolyl.
Scheme 2
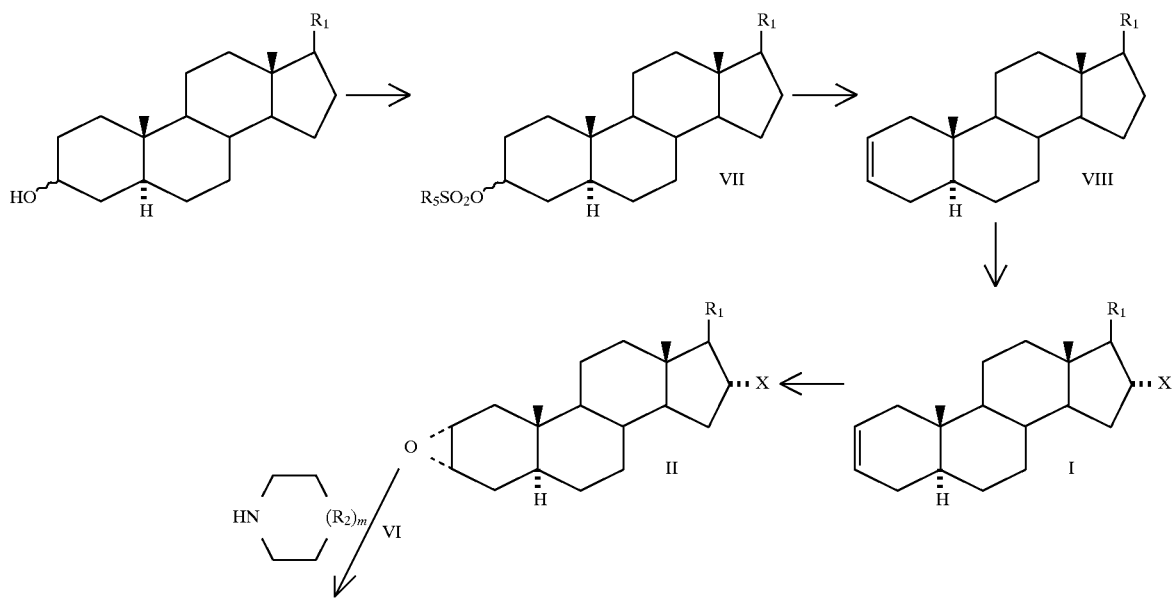

-continued
Scheme 2
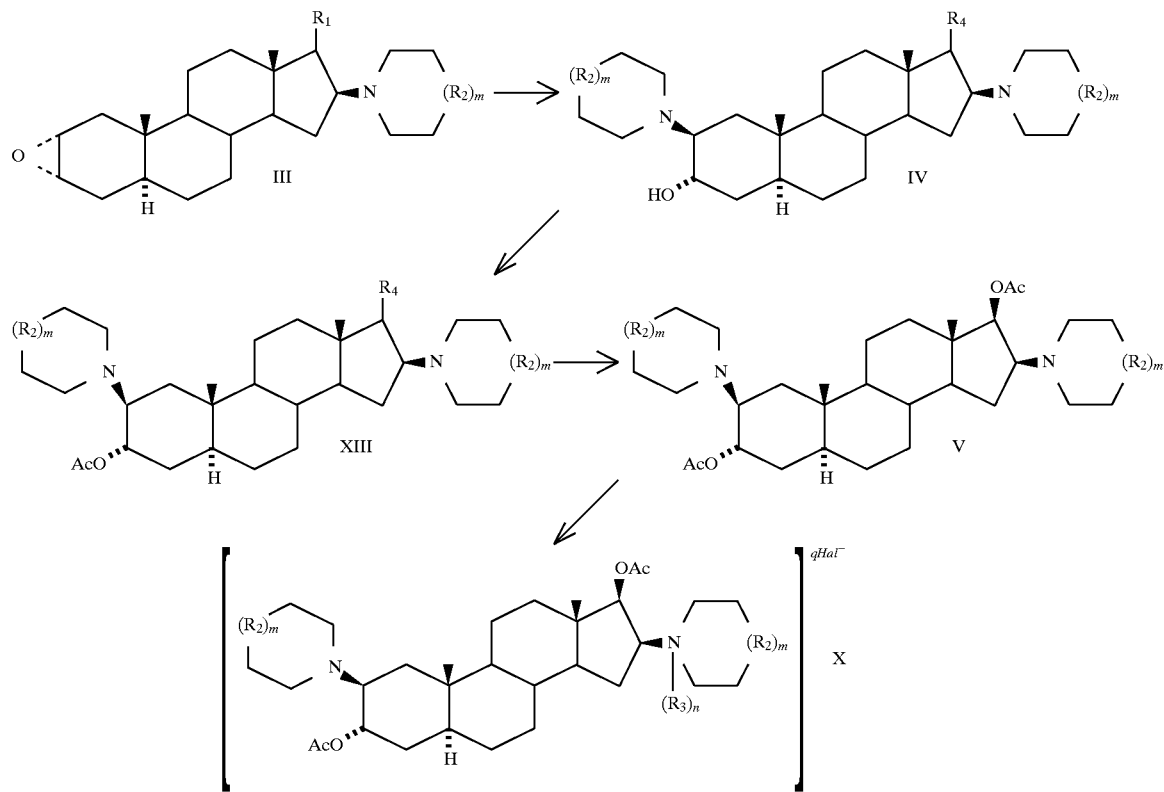
wherein $R_1$, $R_2$, $R_6$, m, $R_3$, n, X, q, and $Hal^-$ are as defined above, $R_4$ is preferably $=O$, and $R_5$ is methyl or p-tolyl.
Scheme 3
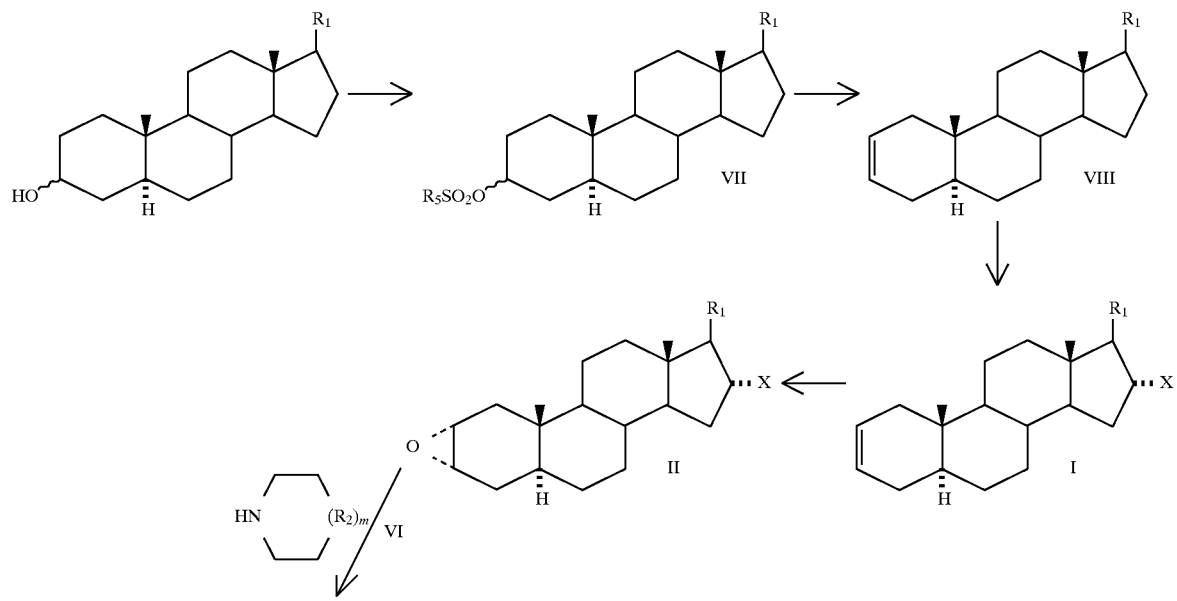

-continued
Scheme 3

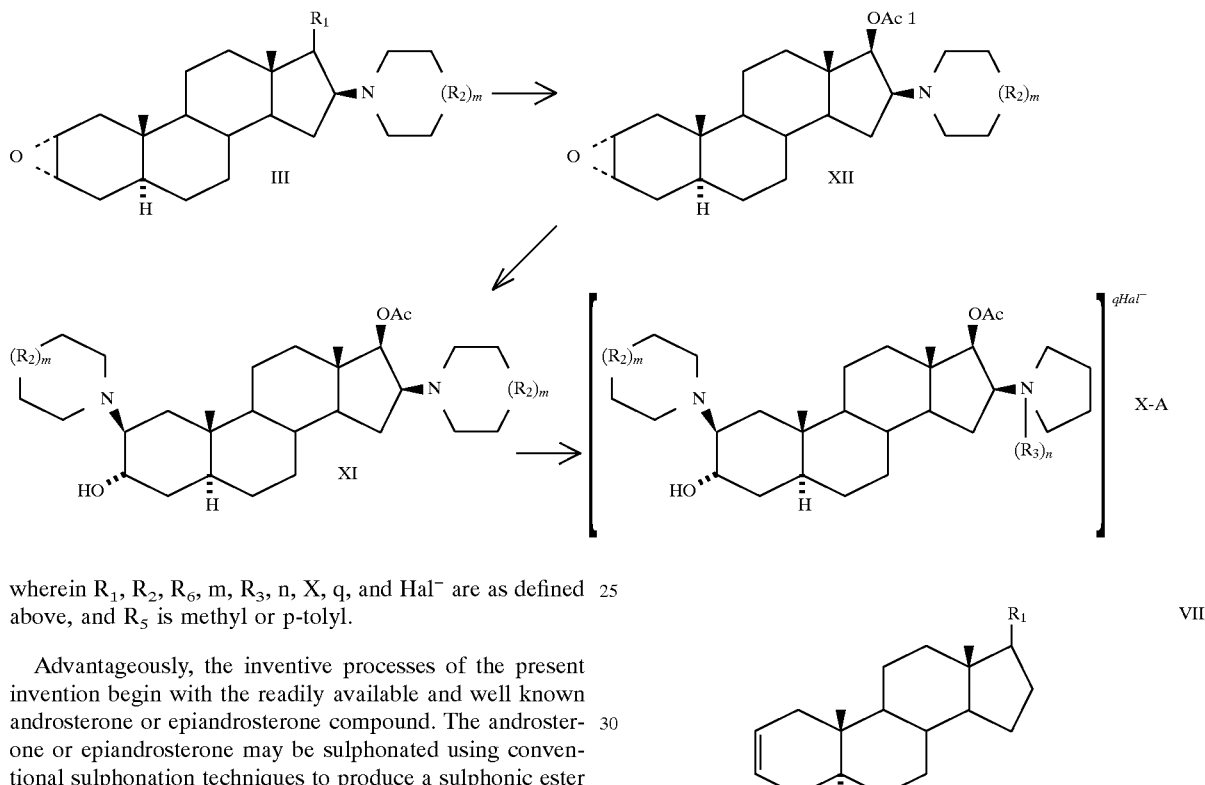

wherein $R_1$, $R_2$, $R_6$, m, $R_3$, n, X, q, and Hal⁻ are as defined above, and $R_5$ is methyl or p-tolyl.

Advantageously, the inventive processes of the present invention begin with the readily available and well known androsterone or epiandrosterone compound. The androsterone or epiandrosterone may be sulphonated using conventional sulphonation techniques to produce a sulphonic ester of androsterone or epiandrosterone of formula VII:

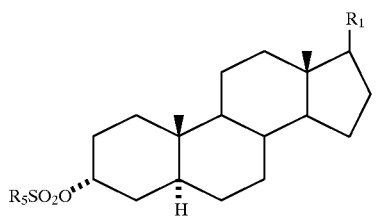

VII wherein $R_5$ is methyl of p-tolyl. More specifically, the androsterone or epiandrosterone may be sulphonated by reacting with a sulphonation reagent such as p-toluenesulphonyl chloride, or methanesulphonyl chloride. Typically, the reaction is carried out in a polar solvent such as pyridine or triethylamine, under ambient temperature and pressure. Preferably, the sulphonic ester of androsterone or epiandrosterone according to formula VII above which is employed in the process of the present invention is the mesylate (i.e., $R_5$ is methyl) or tosylate (i.e., $R_5$ is p-tolyl) sulphonic ester. Currently, the tosylate sulphonic ester of androsterone or epiandrosterone is preferred for the process of the present invention.

The sulphonic esters of androsterone and epiandrosterone are known in the art, and although the foregoing method of preparing these compounds is preferred, other suitable processes of preparing these compounds which are known in the art are also contemplated by the present invention.

The sulphonic ester of formula VII is converted using conventional processes to produce the compounds of formula VIII:

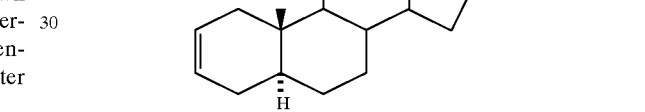

VIII wherein $R_1$ is =O. More specifically, the sulphonic ester of androsterone or epiandrosterone of formula VII may be converted to the compound of formula VIII by reaction with an appropriate alkali metal acetate such as sodium acetate, potassium acetate, and the like in a suitable reaction solvent. Preferably, the reaction solvent comprises acetic acid and acetic anhydride, and the reaction is conducted at reflux under ambient pressure.

The reaction results in the preparation of the compounds of formula VIII in yields exceeding 55%, and often between 65% and 70% based upon the quantity of reactants. In addition, the reaction produces the 3-acetoxy derivative as a side product. A mixture of the two products can advantageously be separated by treatment with potassium hydroxide in methanol. The compound of formula VIII is obtained by crystallization, and the remaining product contains the starting materials androsterone and/or epiandrosterone, which can be recycled in the reaction processes of the present invention without further purification.

The compounds of formula VIII may also be obtained using alternative reaction processes known in the art. According to the second method, compounds of formula VIII may be obtained by adsorption of the sulphonic ester of formula VII on alumina and elution with hexane according to the method described in G. Douglas, et al., *J. Chem. Soc.* 1720–1723 (1959), the disclosure of which is hereby incorporated by reference in its entirety. Advantageously, this method produces the compound of formula VIII in the absence of the 3-acetoxy derivative side product.

The compounds of formula VIII are known in the art, and although the foregoing process of preparing the compounds of formula VIII are preferred, other suitable processes of preparing these compounds are contemplated by the present invention.

The compounds of formula VIII are halogenated with a metal halide to produce the new compounds of formula I:

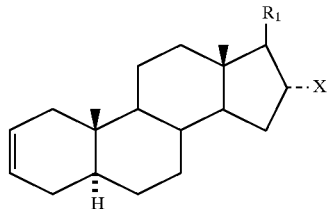

wherein $R_1$ is $=O$ and X is halo. Preferred compounds of formula I include compounds wherein X is bromo. More preferably, the compound of formula I is 5α-androst-2-en-16-α-bromo-17-one.

To produce the compounds of formula I, the compounds of formula VIII are halogenated at position 16 by reaction with a metal halide, preferably a transition metal halide. The halogenation reaction is preferably an α-halogenation reaction whereby a halide is substituted at the 16α position. The halogenation reaction is carried out in an alcoholic solvent at increased temperature and ambient pressure. Suitable alcoholic solvents are known to those skilled in the art and include but are not limited to methanol, ethanol, isopropanol, hexanol, and the like. Methanol is currently the preferred reaction solvent as it is inexpensive and readily available. The reaction is conducted under increased temperature ranging from about 40° C. to about 70° C. up to and including the reflux temperature of the alcoholic solvent. Preferably, the reaction is conducted at about 65° C. the reaction is carried out for a sufficient period of time to effect the halogenation of the compound of formula VIII. Typically, the reaction requires between about 12 and about 36 hours, preferably about 24 hours, for completion.

Suitable metal halides for the conversion of the compounds of formula VIII to the compounds of formula I include but are not limited to fluorides, chlorides, bromides, and iodides of any of copper(II), manganese(II), zinc(II), and the like. Transition metal chlorides and transition metal bromides are the preferred metal halides for the reaction. When metal chlorides are utilized as the metal halide for reaction with the compounds of formula VIII, the reaction is a chlorination reaction at position 16. When metal bromides are utilized as the metal halide, the reaction is a bromination reaction of the compounds of formula VIII at position 16. The preferred metal halide is copper(II)bromide.

If desired, the reaction product of the compound of formula I can be further resolved prior to proceeding with the inventive process, by crystallization using conventional techniques. According to one preferred embodiment, the compound of formula I is crystallized from petroleum ether. Advantageously, the compounds of formula I produced according to the foregoing processes are obtained in yields exceeding 60%, and often reaching between 70% and 80% based upon the quantity of reactants.

The halogenation of the compounds of formula VIII to produce the compounds of formula I was unexpectedly achieved using the foregoing method. The difficulty of halogenating the 16 position, particularly the 16α position of 17-oxo-androstane is well known in the art. See, Elsevier's Encyclopedia of Organic Chemistry, vol. 14, F. radt, ed., Springer Verlag, Berlin, 1959, page 2706s. The chemoselective reactivity between the unsaturation at positions 2—3 of the compound of formula VIII, and the hydrohalide released under the reaction conditions described could not have been anticipated based upon conventional knowledge.

The new compounds of formula I are useful for the preparation of key intermediates in the process of making neuromuscular blocking agents, particularly new intermediate compounds of formula II:

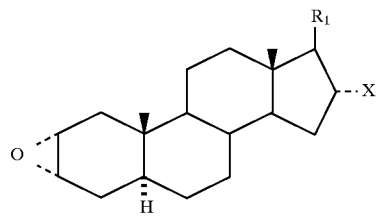

wherein $R_1$ is $=O$ and X is halo at position 16α. Preferred compounds of formula II include those compounds wherein $R_1$ is $=O$ and those compounds wherein X is bromo. More preferably, the compound of formula II is 2α,3α-epoxy-17-oxo,16α-bromo,5α-androstane.

The compounds of formula II can be prepared from the compounds of formula I by reacting the compounds of formula I with a period in a hydrophobic aprotic solvent (e.g., a solvent having a log P value equal to or greater than 0.8). Suitable peracids for reaction with the compounds of formula II include organic peracids such as metachloroperbenzoic acid, t-butylhydroperoxide, p-nitroperbenzoic acid, perbenzoic acid, peracetic acid, and the like. Metachloroperbenzoic acid is currently preferred. Suitable hydrophobic aprotic solvents include but are not limited to methylene chloride, chloroform, hexane, cyclohexane, toluene, benzene, and the like. The reaction is typically initiated at a temperature below about 20° C., preferably about 5° C., and is continued at room temperature after the addition of the peracid is complete, for a period of time sufficient to obtain the compound of formula II. Typically the reaction is continued for between about 6 and 18 hours.

If desired, the reaction products of formula II may be further resolved prior to proceeding with the process of preparing the neuromuscular blocking agents by crystallization using conventional techniques. For example, at the completion of the foregoing reaction, the crude product of formula II thus obtained may be further resolved by crystallization from methanol. Advantageously, the compounds of formula II produced according to the foregoing processes are obtained in yields exceeding 50%, and often reaching between 60% and 75% based upon the quantity of reactants.

As an alternative method of preparing the compounds of formula II, the 16α-substituted compounds of formula II can be prepared by converting a 16β-substituted compounds of formula II-A:

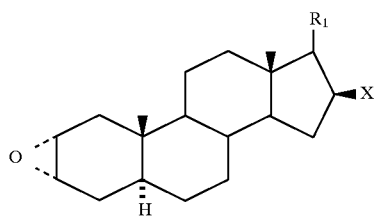

to the 16α epimer. The 16β epimer of formula II-A may be prepared from the known 17β-bromo-2α,3α,16α,17α-diepoxy androstane according to the following Scheme 4:

Scheme 4

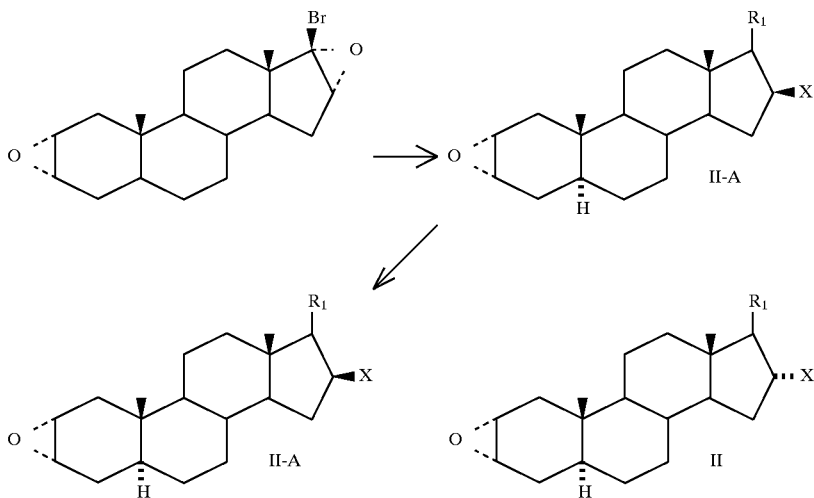

The 16β epimer of Formula II-A is converted to the 16α epimer of Formula II by reaction with acetonitrile and dichloromethane at reflux. Detection of the 16α epimer of Formula I can be accomplished using NMR spectroscopy. In this manner, the 16α epimer of Formula II may be obtained for further reaction in the methods of the present invention.

The compounds of formula II thus obtained can be converted to known neuromuscular blocking agent intermediates of formula III:

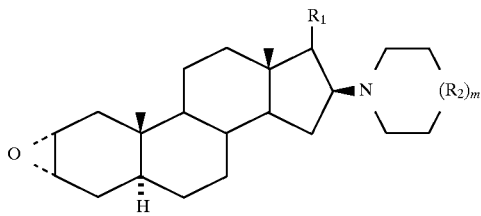

wherein $R_1$ is =O, $R_2$ is >$CH_2$, >$CHR_6$, >$CR_6R_6$, >NH, >$NR_6$, or >O, wherein each $R_6$ is independently lower alkyl, and m is an integer from 0 to 1. Preferred compounds of formula III are those compounds wherein m is 1, and $R_2$ is selected from >$CH_2$ and >$NR_6$ where each $R_6$ is methyl. More preferably, the compound of formula III is a compound wherein m is 1, and $R_2$ is >$CH_2$. The compounds of formula III are known in the art as useful intermediates in processes for preparing diamino androstane neuromuscular blocking agents.

The compounds of formula II are converted to the intermediates of formula III by reacting the compounds of formula II with a compound of formula VI:

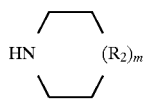

wherein $R_2$, m, and $R_6$ are as defined above. Preferred compounds of formula VI include pyrrolidine, imidazolidine, piperidine, piperazine, morpholine, lower alkyl substituted pyrrolidines, lower alkyl substituted imidazolidines, lower alkyl substituted piperidines, lower alkyl substituted piperazines, and loweralkyl substituted morpholines. In one preferred embodiment, the compound of formula VI is piperidine.

The reaction of the compounds of formula II with the compounds of formula VI is preferably carried out in a organic solvent at elevated temperatures. Suitable organic solvents include but are not limited to acetonitrile, cellosolve, dimethyl sulfoxide, 1,4-dioxide, PEG200, PEG400, toluene, tetrahydrofuran, and the like. The reaction is typically conducted at elevated temperatures ranging from about 60° C. to about 110° C. up to the reflux temperature of the organic solvent chosen. Preferably, the temperature of the reaction is above about 90° C., and more preferalbly about 105° C. The reaction is continued for a period of time sufficient to convert the compounds of formula II to the compounds of formula III. Typically, the reaction requires between about 2 and 4 hours for completion. After the completion of the reaction, the product may be processed prior to continuing with the preparation of the neuromuscular blocking agents if so desired. Suitable processing techniques include solubilization in a solution of hexane and water and extraction with hexane, followed by drying over sodium sulphate. Thereafter the product may be further resolved by crystallization using conventional techniques although it is not required. For example, the compounds of formula III may be crystallized from hexane.

Once obtained, the products of formula III may be converted to the known intermediate compounds of formula IV:

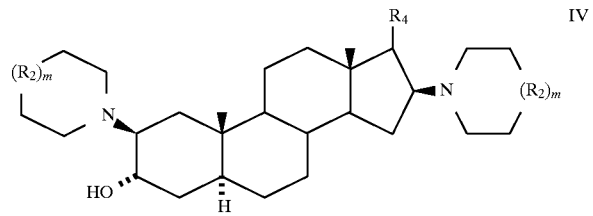

wherein each $R_2$ is independently >$CH_2$, >$CHR_6$, >$CR_6R_6$, >NH, >$NR_6$, or >O, wherein each $R_6$ is independently lower alkyl, each m is independently an integer from 0 to 1, and $R_4$ is =O or H(β-OH), using conventional processes such as the reaction described in U.S. Pat. No. 3,553,212 to Hewett, the disclosure of which is hereby incorporated by reference in its entirety.

Specifically, the compounds of formula III may be converted to compounds of formula IV by reducing the compounds of formula III with a reducing agent to produce a reduced intermediate, and then reacting the reduced intermediate with a compound of formula VI. The reduction reaction of the compound of formula III may be effected using a known reducing agent such as an alkali metal borohydride such as sodium borohydride or potassium borohydride; and an alkali metal trialkoxy borohydride such as sodium trimethoxy borohydride. Sodium borohydride is currently the preferred reducing agent. Alternatively reduction may be accomplished by catalytic hydrogenation according to processes known in the art. The reduction step of the reaction is typically carried out in a solvent selected from polar solvents and mixtures of polar and nonpolar solvents. One preferred reduction solvent comprises methylene chloride:methanol having the ratio of about 1:3. The reaction is typically initiated at a temperature below about 10° C., preferably about 0° C.; and is continued at room temperature after the addition of the reducing agent is complete. The reaction is continued for a period of time sufficient to convert the compounds of formula III to the reduced intermediate product. Typically, the reduction reaction is carried out for between about 1 and about 5 hours.

After the completion of the reduction reaction, the reduced intermediate is reacted with a compound of formula VI to produce the compound of formula IV. As will be appreciated by those skilled in the art, the compound of formula VI utilized in this step may be, but is not required to be the same compound of formula VI as was utilized in the production of compounds of formula III. The reaction of the reduced intermediate with the compound of formula VI may be carried out at reflux for from about 70 to about 90 hours. Thereafter, the compound of formula IV may be crystallized from acetonitrile.

The compounds of formula IV are known as useful intermediates for processes of preparing diamino androstane neuromuscular blocking agents. Although the foregoing method is preferred, other process of producing the compounds of formula IV from the compounds of formula III which are known in the art are also contemplated by the instant invention, and may be employed.

Preferred compounds of formula IV are those compounds wherein $R_4$ is H($\beta$-OH), and compounds wherein each m is 1, and each $R_2$ is selected from >$CH_2$ and >$NR_6$ where $R_6$ is methyl. More preferably, the compound of formula III is a compound wherein $R_4$ is H($\beta$-OH), each m is 1, and each $R_2$ is >$CH_2$.

Once obtained, the compounds of formula IV may be converted to the diamino androstane neuromuscular blocking agents using conventional processes such as those described in U.S. Pat. No. 3,553,212, already incorporated herein by reference. For example, the compounds of formula IV may be converted to the neuromuscular blocking agents according to the following reaction Scheme 5.

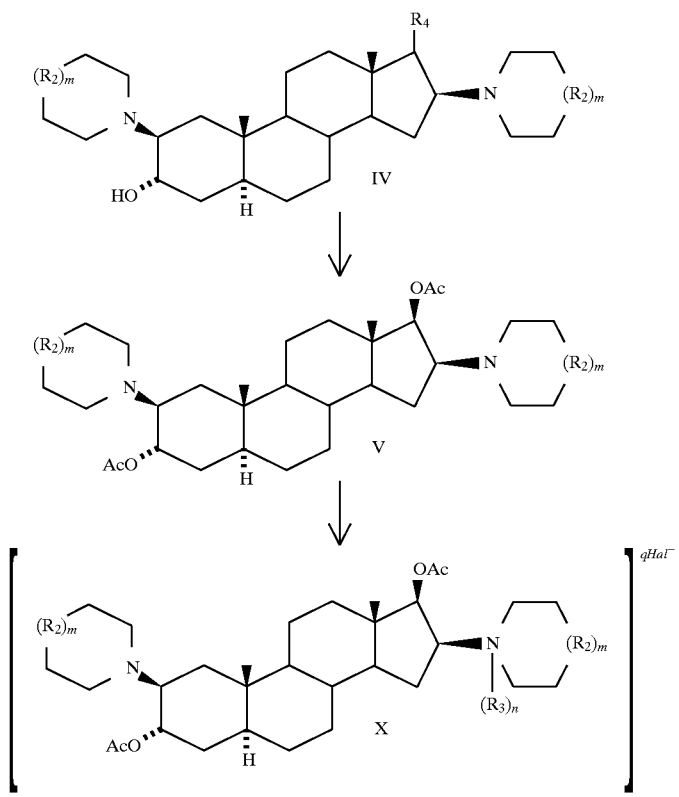

According to Scheme 5, the compounds of formula IV are converted to a diacyloxy intermediate of formula V:

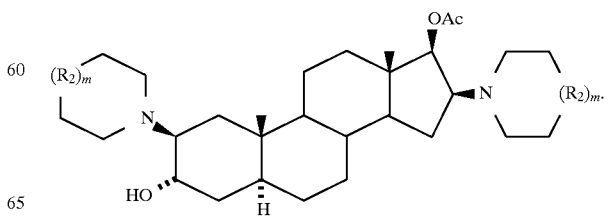

wherein each $R_2$ is independently >$CH_2$, >$CHR_6$, >$CR_6R_6$, >NH, >$NR_6$, or >O, wherein each $R_6$ is independently lower alkyl, each m is independently an integer from 0 to 1. Preferred compounds of formula V are those compounds wherein, and compounds wherein each m is independently 1, and each $R_2$ is independently selected from >$CH_2$ and >$NR_6$ wherein each $R_6$ is methyl. More preferably, the compound of formula V is a compound wherein each m is 1, and each $R_2$ is >$CH_2$.

The conversion of the compound of formula IV to the diacyloxy intermediate of formula V may be achieved by acylating the compound of formula IV with an acylating agent selected from the group consisting of $C_{1-5}$ aliphatic carboxylic acid, $C_{1-5}$ aliphatic carboxylic anhydride, and $C_{1-5}$ aliphatic carboxylic acid halogenide, and mixtures thereof. Preferred acylating agents include acetic acid, acetic anhydride, mixtures of acetic acid and acetic anhydride, and propionic acid anhydride.

The diacyloxy intermediate of formula V is then readily converted to the neuromuscular blocking agents of formula X by converting the diacyloxy intermediate to a mono- or di-quaternary amine salt or an acid addition salt thereof. The mono- or di-quaternary amine salts or acid addition salts may be obtained using the process described in U.S. Pat. No. 3,553,212 to Hewitt or U.S. Pat. No. 4,071,414 to Tuba et al., the disclosures of which are incorporated herein by reference in their entirety. More specifically, the mono- and di-quaternary amine salts may be obtained by reacting the diacyloxy intermediate of formula V with an alkyl halide such as methyl bromide, methyl iodide, ethyl bromide, ethyl iodide, or propylene bromide. The acid addition salts may be obtained by reacting the diacyloxy intermediate of formula V with an organic or inorganic acid such as hydrofluoric acid, hydrochloric acid, hydrobromic acid, hydroiodic acid, citric acid, or pyruvic acid.

Alternatively, the compounds of formula III may be converted to the neuromuscular blocking agents of formula X by a second route. In particular, the compounds of formula III are reacted with a compound of formula VI to produce a compound of formula IV wherein $R_4$ is preferably =O. The reaction of the compound of formula III with the compound of formula VI is carried out at reflux for from about 70 to about 90 hours, as is described hereinabove. This embodiment differs from that previously described in that in this embodiment, the compound of formula III is not reduced prior to reaction with the compound of formula VI.

The compound of formula IV wherein $R_4$ is =O, which is produced from the reaction is then acylated with an acylating agent as described in the previous embodiment. The acylation reaction produces a monoacyloxy intermediate of formula XIII as shown in Scheme 2 hereinabove. The monoacyloxy intermediate is then reduced using a reducing agent as described hereinabove, and the then reduced intermediate is again acylated with an acylating agent to produce the diacyloxy intermediate of formula V. The diacyloxy intermediate is then converted to the neuromuscular blocking agent of formula X in the manner described hereinabove.

In another embodiment, the compounds of formula III may be converted to neuromuscular blocking agents of formula X-A:

wherein $R_2$, m, $R_3$, n, q, and $Hal^-$ are as defined hereinabove. Particularly preferred neuromuscular blocking agents of formula X-A include compounds of formula X-A wherein m is 1, $R_2$ is >O, n is 1, and $R_3$ is propyl. According to this embodiment of the present invention, the compounds of formula III are reduced with a reducing agent as described hereinabove. Thereafter, the reduced intermediate is acylated with an acylating agent as described hereinabove to produce the monoacyloxy intermediate (see the compound of formula XII of Scheme 3). This monoacyloxy intermediate is then reacted with a compound of formula VI to produce a compound of formula XI:

wherein $R_2$ and m are as defined hereinabove. The compound of formula XI may then be converted to the neuromuscular blocking agent of formula X-A by reacting with an alkyl halide as described hereinabove.

According to one particularly preferred embodiment of the present invention, the neuromuscular blocking agents vecuronium bromide or pancuronium bromide are prepared using the new intermediate compounds of formulas I and II. The process comprises the steps of a) reacting the compound of Formula I with metachloroperbenzoic acid in methylene chloride to produce a compound of Formula II; b) reacting the compound of Formula II with piperidine to produce the compound of Formula III; c) reducing the compound of Formula III with sodium borohydride to produce a reduced intermediate; d) reacting the reduced intermediate with piperidine to produce a compound of Formula IV; e) acylating the compound of Formula IV with an acylating agent selected from the group consisting of acetic acid, acetic anhydride, and mixtures thereof, to produce a diacyloxy intermediate; and f) converting the diacyloxy intermediate to a mono- or di-quaternary amine salt thereof to produce vecuronium bromide or pancuronium bromide.

The following examples are provided to illustrate the present invention, and should not be construed as limiting thereof. In these examples, "g" means grams, "mg" means milligrams, "ml" means milliliters, "mmoles" means millimoles, and "°C." means degrees Centigrade.

EXAMPLE 1

Preparation of Tosyl Derivative of Epiandrosterone p-Toluenesulphonyl chloride (100 g) is added to a solution of epiandrosterone (100 g, 0.344 moles) in 250 ml pyridine, and the resulting solution is left at room temperature overnight. The reaction mixture is poured into water and ice and the precipitate so obtained is filtered and washed abundantly with water. The tosyl derivative (144 g 0.315 moles) is recovered in 92% yield.

Elemental analysis for tosyl derivative ($C_{26}H_{36}O_4S_1$): theoretical H:8.17%, C:70.23%, S:7.20%; found H:7.22%, C:70.28%, S:7.23%.

$^1$H-NMR analysis (60 MHz $CDCl_3$): δ0.8 (s, 6H, 2$CH_3$), 2.45 (s, 3H, $CH_3$—Ar), 4.5–4.75 (m, 1H, —CH—O), 7.5 (d, 2H, aromatic), 8.0 (d, 2H, aromatic).

EXAMPLE 2

Preparation of 5-α-androst-2-en-17-one from Tosyl Derivative

The tosyl derivative of Example 1 (45.5 g; 102.42 mmoles) is added to a mixture of acetic acid (422 ml), acetic anhydride (42.25 ml) and sodium acetate (47.12 g). The reaction mixture is refluxed and processed for two hours. Thereafter the mixture is extracted with chloroform (3×30 ml), and washed first with a sodium carbonate solution and then with water. A crude mixture (30.7 g) of the desired product 5α-androst-2-en-17-one and the acetate derivative thereof is obtained. The crude mixture is hydrolyzed under reflux conditions in a mixture of methanol (930 ml), water (140 ml) and potassium hydroxide (18.6 g). After refluxing for 30 minutes, the reaction is agitated at room temperature for 8–10 hours. The precipitate obtained is recovered by filtration and dried under vacuum to give 12.2 g (44.78 mmoles; 43% yield) of 5α-androst-2-en-17-one.

The mother liquors recovered from the crystallization, are concentrated to dryness to give a residue. The residue is dissolved with water, and extracted with methylene chloride. And after evaporation of the organic phase, crude androsterone (14.7 g; 50.61 mmoles) is obtained.

Elemental analysis for 5α-androst-2-en-17-one ($C_{19}H_{28}O_1$): theoretical H:10.36%, C83.77%; found H:10.34%, C:83.73%. Infra red analysis ($CHCl_3$): 3020, 2971, 1731 cm$^{-1}$.

$^1$H-NMR analysis (60 MHz $CDCl_3$): δ0.8 (s, 3H, $CH_3$), 0.9 (s, 3H, $CH_3$), 5.7 (s, 2H, —CH=CH—).

EXAMPLE 3

Preparation of 5α-androst-2-en-17-one from Tosyl Derivative

The tosyl derivative of Example 1 (1 g, 2.25 mmoles) is dissolved in 30 ml n-hexane and adsorbed on a basic alumina column (100 g). After 18 hours, the column is eluted with hexane. 5α-Androst-2-en-17-one (441 mg, 1.62 mmoles, 72% yield) is recovered as the only product. The chemophysical properties of the product recovered are the same as reported in Example 2.

EXAMPLE 4

Preparation of 5α-androst-2-en-16-α-bromo-17-one from 5α-androst-2-en-17-one

5α-Androst-2-en-17-one (20 g, 73.41 mmoles) is dissolved with stirring at room temperature, in 1.6:1 of methanol. Copper (II) bromide (32.93 g, 147.43 mmoles) is added to this solution with stirring at room temperature. The reaction is refluxed with stirring for 24 hours. Thereafter the reaction is cooled to room temperature, and the inorganic salts are removed by filtration. The filtrate is concentrated under vacuum to give a residue which is washed with water and extracted with methylene chloride. The organic extracts are dried over sodium sulphate, filtered and concentrated under vacuum to give a residue from which 5α-androst-2-en-16α-bromo-17-one (19.2 G, 54.65 mmoles; 74.4% yield) is recovered by crystallization with petroleum ether.

Elemental analysis for 5α-androst-2-en-16α-bromo-17-one ($C_{19}H_{27}O_1Br_1$): theoretical H:7.75%, C:64.96%, Br:22.74%; found H:7.71%, C:64.94%, Br:22.73%. Mass Spectrometry Analysis (m/e): 353 (M+2), 352 (M+1), 351 (M+1), 272 (M−79), 271 (M−80). Infra red Analysis ($CHCl_3$): 3020, 2970, 1748 cm$^{-1}$. $[α]_D$=+100.5; $[α]_{546}$=+125.3 (c=1 $CHCl_3$), MP=147° C.

EXAMPLE 5

Preparation of 2α,3α-epoxy-17-oxo,16α-bromo,5α-androstane from 5α-androst-2-en-16α-bromo-17-one 5α-Androst-2-en-16α-bromo-17-one (15 g, 42.69 mmoles) is dissolved in anhydrous methylene chloride (300 ml) and the solution obtained is cooled to 5° C. Thereafter 90 ml of a solution of metachloroperbenzoic acid (11.65 g, 70%) in methylene chloride is added slowly, maintaining constant reaction temperature. The reaction is then stirred at room temperature for 8 hours. Thereafter the reaction is processed by washing the organic phase with 5% ammonia followed by water, to neutrality. The organic phase is dried over sodium sulphate, filtered and evaporated under vacuum to give 16 g of an oily residue from which 10.5 g (28.58 mmoles; 67% yield) of 2α,3α-epoxy-17-oxo-16α-bromo, 5α-androstane is recovered by crystallization from methanol.

Elemental analysis calculated for 2α,3α-epoxy-17-oxo-16α-bromo,5α-androstane ($C_{19}H_{27}O_2Br_1$): theoretical H:7.41%, C:62.13%, Br:21.75%; found H:7.44%, C:62.10%, Br:21.72%. Mass Spectrometry Analysis (m/e): 369 (M+2), 368 (M+1), 367 (M+1), 352 (M−15), 288 (M−79) 287 (M−80). $[α]_D$=+68 $[α]_{546}$=+86.1 (c=1 $CHCl_3$), MP=134° C.

EXAMPLE 6

Preparation of 2α,3α-epoxy-17-oxo,16β-piperidine, 5α-androstane from 2α,3α-epoxy-17-oxo,16α-bromo-5α-androstane 2α,3α-Epoxy-17-oxo,16α-bromo-5α-androstane (9 g, 24.50 mmoles) is dissolved at room temperature in a mixture of 150 ml acetonitrile and 9.9 ml piperidine. The reaction mixture is refluxed for 3 hours, and then evaporated to dryness under vacuum. The residue is dissolved in a hexane/water mixture. The organic phase is separated and the aqueous phase is extracted twice with hexane. The collected organic phases are then dried over sodium sulphate, filtered and vacuum evaporated to produce 8.9 g (23.95 mmoles) of unpurified single-spot material (TLC $CHCl_3$:methanol (9:1) with 2% of a 30% ammonia solution) which is used without further purification in the next step of the reaction. For analytical purposes, a sample of the product was purified by crystallization from hexane.

Elemental analysis for 2α,3α-epoxy-17-oxo,16α-piperidine-5α-androstane ($C_{24}H_{37}N_1O_2$): theoretical H:10.04%, C:77.58%, N:3.77%; found H:10.07%, C:77.61%, N:3.72%. Mass Spectrometry Analysis (m/e): 373 (M+2), 372 (M+1), 371 (M+1), 356 (M−15), 288 (M−83), 272 (M−99).

$^1$H-NMR (500 MHz, $CDCl_3$): δ0.74 (s, 3H, 18-$CH_3$), 0.79 (s, 3H, 19-$CH_3$), 2.37–2.43 and 2.56–2.63 (2m, 4H, —CH$_2$—N—CH$_2$—), 2.99–3.12 (complex system, 3H, CH—O—CH— and 16α-CH).

EXAMPLE 7

Preparation of 2α,3α-epoxy-17β-hydroxy,16β-piperidine-5α-androstane from 2α,3α-epoxy-17-oxo,16β-piperidine,5α-androstane Sodium borohydride (0.77 g) is added portionwise to a solution of 0.93 g (2.50 mmoles) of the intermediate 2α,3α-epoxy-17-oxo,16β-piperidine,5α-androstane in 3 ml methylene chloride and 8 ml methanol with stirring at 0° C. keeping the temperature of the reaction constant. After addition of all of the sodium borohydride, stirring is continued at room temperature for 6 hours. The organic phase is then evaporated with vacuum. The residue obtained is redissolved in CHCl$_3$ and washed with a 2% NaOH solution. The organic phase is separated and washed with water to neutrality and then dried over sodium sulphate, filtered and evaporated under vacuum to give a crude product with which 0.6 g (1.60 mmoles; 64% yield) of 2α,3α-epoxy-17β-hydroxy,16β-piperidine,5α-androstane is recovered by crystallization from methanol.

Elemental analysis for 2α,3α-epoxy-17β-hydroxy,16β-piperidine,5α-androstane (C$_{24}$H$_{39}$N$_1$O$_2$): theoretical H:10.52%, C:77.16%, N:3.75%; found H:10.48%, C:77.11%, N:3.70%. Mass Spectrometry Analysis (m/e): 374 (M+1), 373 (M+1), 372 (M-1), 358 (M-15), 355 (M-18), 344 (M-29), 290 (M-83). Infra Red Analysis (CH$_2$Cl$_2$): 3290.9, 2934.9, 2850.5 cm$^{-1}$.

$^1$H-NMR (500 MHz CHCl$_3$): δ0.62 (s, 3H, 18-CH$_3$), 0.73 (s, 3H, 19-CH$_3$), 2.37–2.55 (broad, 4H, CH$_2$—N—CH$_2$—), 2.72 (dd, 1H, 16α-CH), 3.12 and 3.07 (2m, 2H, —CH—O—CH), 3.35 (d, 9 Hz, 1H, 17α-CH).

EXAMPLE 8

Preparation of 2β,16β-bis-piperidin-3α,17β-dihydroxy-5α-androstane from 2-α,3α-epoxy-17β-hydroxy,16β-piperidine,5α-androstane A solution of 2α,3α-epoxy-17β-hydroxy,16β-piperidine,5α-androstane (0.5 g; 1.34 mmoles) in piperidine (0.825 ml) and water (0.07 ml) is refluxed for 70 hours. The reaction solvent is evaporated by vacuum. The crude product so obtained is purified by crystallization from acetonitrile to yield 0.28 g (0.61 mmoles; 45.60% yield) of 2β,16β-bis-piperidin-3α,17β-dihydroxy-5α-androstane.

Elemental analysis for 2β,16β-bis-piperidin-3α,17β-dihydroxy-5α-androstane (C$_{29}$H$_{50}$N$_2$O$_2$): theoretical H:10.99%, C:75.93%, N:6.11%; found H:10.95%, C:75.92%, N:6.08%. Mass Spectrometry (m/e): 459 (M+1), 458 (M+1), 457 (M-1), 443 (M-15), 440 (M-18), 429 (M-29), 375 (M-83), 344 (M-114).

$^1$H-NMR (500 MHz, CDCl$_3$): δ0.69 (s, 3H, 18-CH$_3$), 0.80 (s, 3H, 19-CH$_3$), 1.20–1.30 (m, 1H, 15β-CH), 1.75–1.85 (m, 1H, 4-CH), 1.85–1.90 (m, 1H, 12β-CH) 2.25–2.33 (s, broad, 2H, CH$_2$—N—), 2.40–2.65 (complex system, 7H,—CH$_2$—N—, (CH$_2$)—$_2$N— and 2α-CH—), 2.75 (dd, 1H, 16α-CH), 3.35 (d, 9 Hz, 1H, 17α-CH), 3.72–3.80 (m, 1H, 3β-CH).

EXAMPLE 9

Preparation of 2α,3α-epoxy-16β-bromo-androstan-17-one

2α,3α,16α,17α-diepoxy-17β-bromo androstane (1 g) is dissolved in 10 ml of acetonitrile and 1.1 ml of pyridine. The reaction mixture is maintained under stirring at room temperature for 25 hours. Thereafter, the mixture is evaporated under vacuum at 40° C. to afford 1.21 g of crude reaction product which is purified by acetone crystallization to afford 800 mg of pure 2α,3α-epoxy-16β-bromo-androstan-17-one. [α]$_D$=+124 (c=1 CHCl$_3$).

EXAMPLE 10

Epimerization of 2α,3α-epoxy-16β-bromo-androstan-17-one to Form 2α,3α-epoxy-16α-bromo-androstan-17-one 2α,3α-Epoxy-16β-bromo-androstan-17-one (0.5 g) is dissolved in acetonitrile (5 ml) and dichloromethane (1 ml). The reaction mixture is refluxed for 192 hours checking the epimerization by nuclear magnetic resonance spectroscopy (diagnostic signal of 16CH: 16α-bromo=3.9 ppm; 16β-bromo=4.4 ppm). After one hour of reaction, the ratio of 16α:16β is 5:95. After 72 hours of reaction the ratio of 16α:16β is 28:72. After 96 hours of reaction the ratio of 16α:16β is 35.65. After 168 hours of reaction the ratio of 16α:16β is 41.59. After 172 hours the ratio of 16α:16β is 40:60. The 16α and 16β epimers may be separated by silica gel chromatography using hexane:ethyl acetate=8:2.

The foregoing is illustrative of the present invention and is not to be construed as limiting thereof. The invention is defined by the following claims, with equivalents of the claims to be included therein.

That which is claimed is:

1. A compound of Formula I:

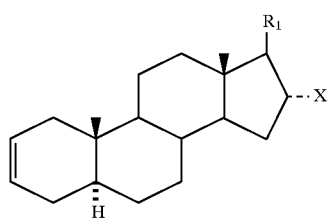

wherein:

R$_1$ is =O and X is halo.

2. The compound according to claim 1, wherein X is Br.

3. A compound of Formula II:

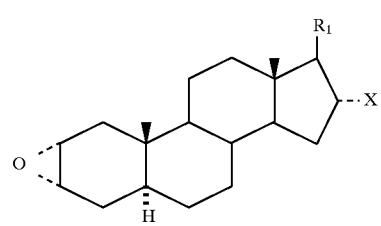

wherein:

R$_1$ is =O and X is halo.

4. The compound according to claim 3, wherein X is Br.

5. A process for preparing a compound of Formula I:

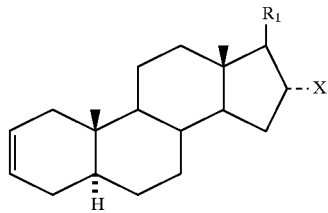

wherein:

$R_1$ is =O and X is halo, said process comprising 16α-halogenating a compound of Formula VIII:

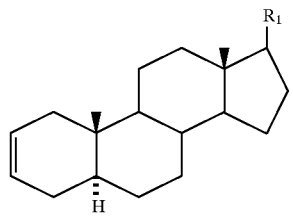

with copper(II)halide to produce said compound of Formula I.

6. The process according to claim 5, wherein said copper(II)halide is copper(II)bromide, and X is Br.

7. The process according to claim 5, wherein said step of 16α-halogenating is carried out at about 90° C.

8. The process according to claim 5 further comprising the step of crystallizing said compound of Formula I.

9. The process according to claim 8, wherein said step of crystallizing comprises crystallizing said compound of Formula I from ether.

10. The process according to claim 5 further comprising the step of reacting a sulphonic ester of androsterone or epiandrosterone with sodium acetate in the presence of reaction solvent comprising acetic acid and acetic anhydride to produce said compound of Formula VIII prior to said step of 16α-halogenating.

11. A process for preparing a compound of Formula II:

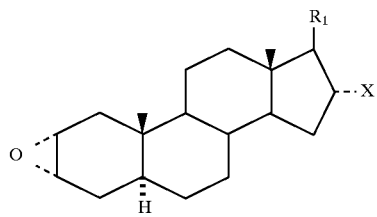

wherein $R_1$ is =O and X is halo, said process comprising reacting a compound of Formula I:

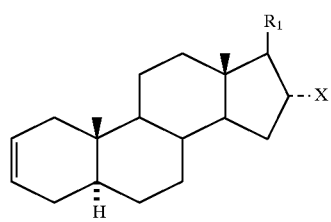

with a peracid in a hydrophobic aprotic solvent.

12. The process according to claim 11, wherein said peracid is selected from the group consisting of metachloroperbenzoic acid, t-butylhydroperoxide, p-nitroperbenzoic acid, perbenzoic acid, and peracetic acid.

13. The process according to claim 11, wherein said hydrophobic aprotic solvent is selected from the group consisting of methylene chloride, chloroform, hexane, cyclohexane, toluene, and benzene.

14. The process according to claim 11, wherein said peracid is metachloroperbenzoic acid.

15. The process according to claim 11, wherein said hydrophobic aprotic solvent is methylene chloride.

16. The process according to claim 11, wherein X is Br.

17. The process according to claim 11, further comprising the step of 16α-halogenating a compound of Formula VIII:

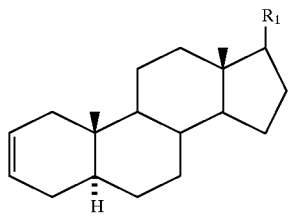

with copper(II)halide to produce said compound of Formula I prior to said step of reacting said compound of Formula I.

18. The process according to claim 17 further comprising the step of crystallizing said compound of Formula I prior to said step of reacting said compound of Formula I.

* * * * *